United States Patent
Lin et al.

(10) Patent No.: US 7,489,403 B1
(45) Date of Patent: Feb. 10, 2009

(54) ELECTRONIC TESTING APPARATUS AND TESTING METHOD THEREOF

(75) Inventors: Chien-Der Lin, Sinshih Township, Tainan County (TW); Wen-Chung Hsu, Sinshih Township, Tainan County (TW); Tsung-Kai Chuang, Sinshih Township, Tainan County (TW); Jiann-Hua Wang, Sinshih Township, Tainan County (TW)

(73) Assignee: Kaiwood Technology Co., Ltd., Sinshih Township (TW)

( * ) Notice: Subject to any disclaimer, the term of this patent is extended or adjusted under 35 U.S.C. 154(b) by 0 days.

(21) Appl. No.: 12/073,880

(22) Filed: Mar. 11, 2008

(30) Foreign Application Priority Data

Nov. 26, 2007 (TW) .............................. 96144856 A

(51) Int. Cl.
*G01N 21/84* (2006.01)
(52) U.S. Cl. ....................................... 356/429; 356/947
(58) Field of Classification Search .................. 33/543; 436/158, 164, 50, 55; 702/19; 422/58, 82.05, 422/67; 435/288.7; 356/429–430, 255, 369, 356/132, 612, 947
See application file for complete search history.

(56) References Cited

U.S. PATENT DOCUMENTS 7,214,542 B2 * 5/2007 Hutchinson ................. 436/164

* cited by examiner

*Primary Examiner*—Gregory J Toatley, Jr.
*Assistant Examiner*—Tri T Ton
(74) *Attorney, Agent, or Firm*—Birch, Stewart, Kolasch & Birch, LLP

(57) ABSTRACT

An electronic testing apparatus is provided. The electronic testing apparatus includes a testing paper having a first reaction line and a second reaction line; a circuit board, having a light source, a first detector, a second detector equipped thereon, the light source being disposed between the first detector and the second detector; and a light shelter, defining a first chamber, a second chamber, and a third chamber, in which there is a first slit configured between the first chamber and the second chamber, and a second slit configured between the second chamber and the third chamber. The first chamber, the second chamber, and the third chamber respectively shelter the first detector, the light source, and the second detector. The first detector detects a reflected light of the light projected to the first window through the first slit by the light source, and the second detector detects a reflected light of the light projected to the second window through the second slit by the light source.

13 Claims, 6 Drawing Sheets

ELECTRONIC TESTING APPARATUS AND TESTING METHOD THEREOF

BACKGROUND OF THE INVENTION

1. Field of the Invention

The present invention relates generally to an electronic testing apparatus and a testing method thereof, which are adapted for fast testing variation of reaction line so as to drastically improve a testing efficiency.

2. The Prior Arts

Biochemistry inspection has become a routine item of body check. However, a result of a biochemistry inspection may vary according to factors of the operators. For example, a urine pregnancy test reagent which is widely sold in the market is adapted for testing a concentration of human chorionic gonadotropin (HCG) existed in urine. The reagent is adapted for an immunity inspection method mainly relying upon a chromatography inspection, in corporation with the specific binding between antigens and antibodies, to directly identify an inspection result by naked eyes. However, reading results by naked eyes often cause error. Especially when a single color reaction line is light and blur, different operators may obtain different testing results.

Correspondingly, there has been developed an electronic testing apparatus. As shown in FIG. 1, there is shown an isometric view of such an electronic testing apparatus. The electronic testing apparatus includes a housing 1 and a lid 15. The housing 1 has a display 11 disposed thereon for displaying a digital detection result. The lid 15 includes an absorber. In operation, the user removes the lid 15 from the housing 1, and dips the absorber in the sample, e.g., urine, for 15 to 20 seconds. And then the user lids the lid back to prevent a leakage therefrom. After several minutes, a detection result will be displayed on the display showing that whether the user is pregnant.

Referring to FIG. 2, there are shown internal components of a conventional electronic testing apparatus. As shown in FIG. 2, the conventional electronic testing apparatus includes a testing paper 200, a light shelter 210, and a circuit board 220. The testing paper 200 has an end fixed to the light shelter 210, and another end connected to an absorber. The testing paper includes a C line and a T line. The C line represents a control line, and the T line represents a testing line. The C line reflects a quality and concentration standard of the test item. The light shelter 210 includes a light sheltering mask 211, and three windows 212. The circuit board 220 includes an IC controller 223 and three light sources 221 disposed thereon. There are two light detectors 222 correspondingly disposed beneath the first light source and the third light source, respectively. The light sheltering mask 211 of the light shelter 210 shelters the three light sources 221 and the two light detectors 222. The three windows 212 of the light sheltering mask 211 configure three light sheltering chambers, respectively. The three light sheltering chambers respectively and correspondingly shelter the three light sources 221, so as to prevent interference to the light detectors 222 by adjacent light. Further, there are three windows 212 configured at the light sheltering chambers, in correspondence to three upper openings of the three light sources.

The testing paper 200 is positioned on the light shelter 210. The C line and the T line of the testing paper 200 are aligned to the first and the third windows 212, respectively, so as to allow light from the first light source and light from the third light source to illuminate on the C line and the T line, respectively. The two light detectors 222 test light reflected from the C line and the T line. The IC controller 223 receives a detection signal from the light detector 222 for determining response statuses of the C line and the T line.

However, such the conventional electronic testing apparatus disadvantageously requires three light sources, which require much cost. Further, the light sheltering mask of the light shelter is required to configure three individual spaces which shelters light from the others. Such light sheltering chamber structure is complicated, and need to be further improved.

SUMMARY OF THE INVENTION

A primary objective of the present invention is to provide an electronic testing apparatus, which is adapted to use one light source to test two reaction lines.

Another objective of the present invention is to provide a method for applying the electronic testing apparatus. The method adaptively arranges the light sources and the light detectors, so as to advantageously test the reflective light signal of the reaction line and maintain an accuracy of the detection.

For achieving the foregoing objectives, the present invention provides an electronic testing apparatus. The electronic testing apparatus includes a testing paper having a first reaction line and a second reaction line; a circuit board, having a light source, a first detector, a second detector equipped thereon, the light source being disposed between the first detector and the second detector; and a light shelter, defining a first chamber, a second chamber, and a third chamber, in which there is a first slit configured between the first chamber and the second chamber, and a second slit configured between the second chamber and the third chamber. The first chamber, the second chamber, and the third chamber respectively shelter the first detector, the light source, and the second detector. The first detector detects a reflected light of the light projected to the first window through the first slit by the light source, and the second detector detects a reflected light of the light projected to the second window through the second slit by the light source.

The present invention further provides a testing method for the electronic testing apparatus. The testing method includes: providing a light source positioned between a first detector and a second detector; disposing a first chamber, a second chamber, and a third chamber respectively sheltering the first detector, the light source, and the second detector, in which a first slit is configured between the first chamber and the second chamber, and a second slit is configured between the second chamber and the third chamber; the first detector detecting a reflected light of a light projected by the light source on the first reaction line, through the first slit; and the second detector detecting a reflected light of a light projected by the light source on the second reaction line, through the second slit.

The electronic testing apparatus is simple and convenient for assembling. It employs only one light source, and two detectors, and thus saving production cost and improving efficiency. The testing method for the electronic testing apparatus adopts a specific arrangement of the light source and the detectors for more advantageously detecting the reflecting light signal from the reaction lines, and thus improving the test accuracy.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the present invention, and are incorporated in and constitute a part of this specification. The drawings illustrate embodiments of the invention and, together with the description, serve to explain the principles of the present invention.

Figure 1:
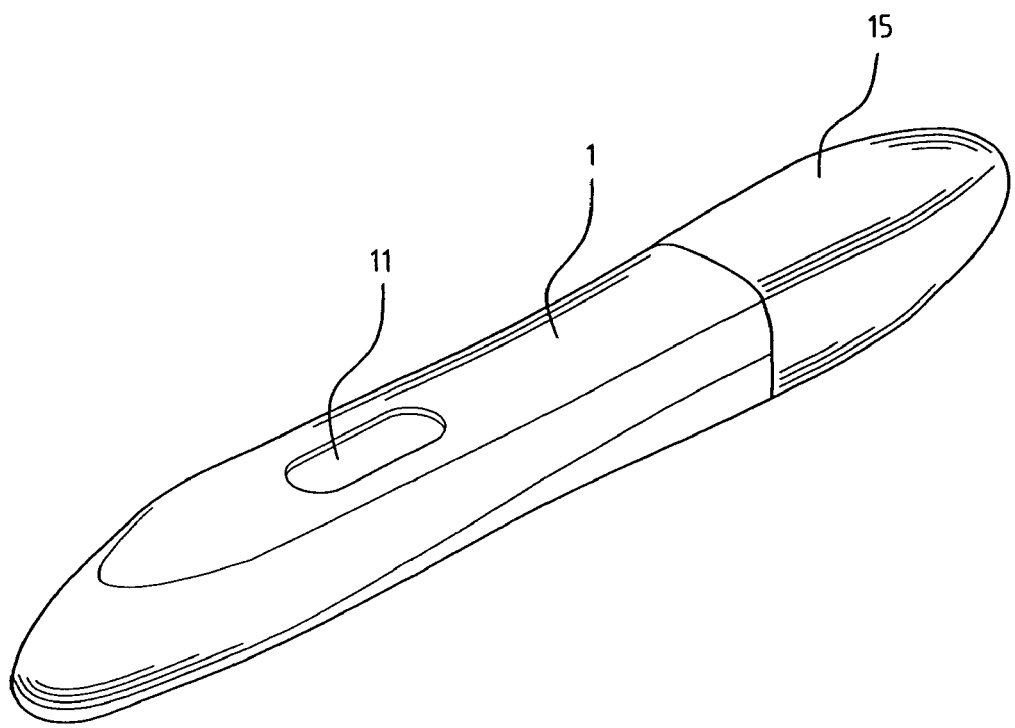
FIG. 1 is an isometric view of a conventional electronic testing apparatus.
Figure 2:
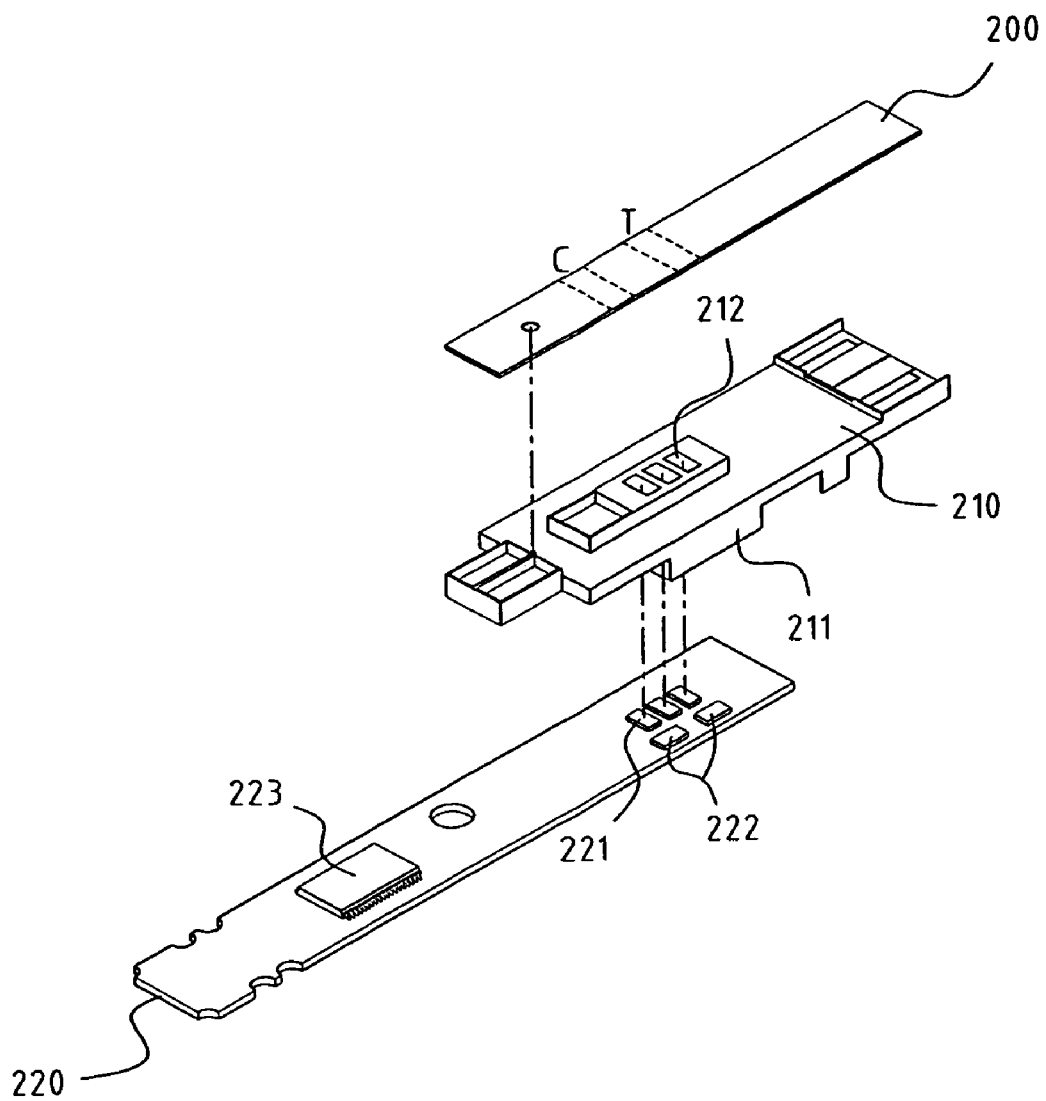
FIG. 2 illustrates internal components of a conventional electronic testing apparatus.
Figure 3:
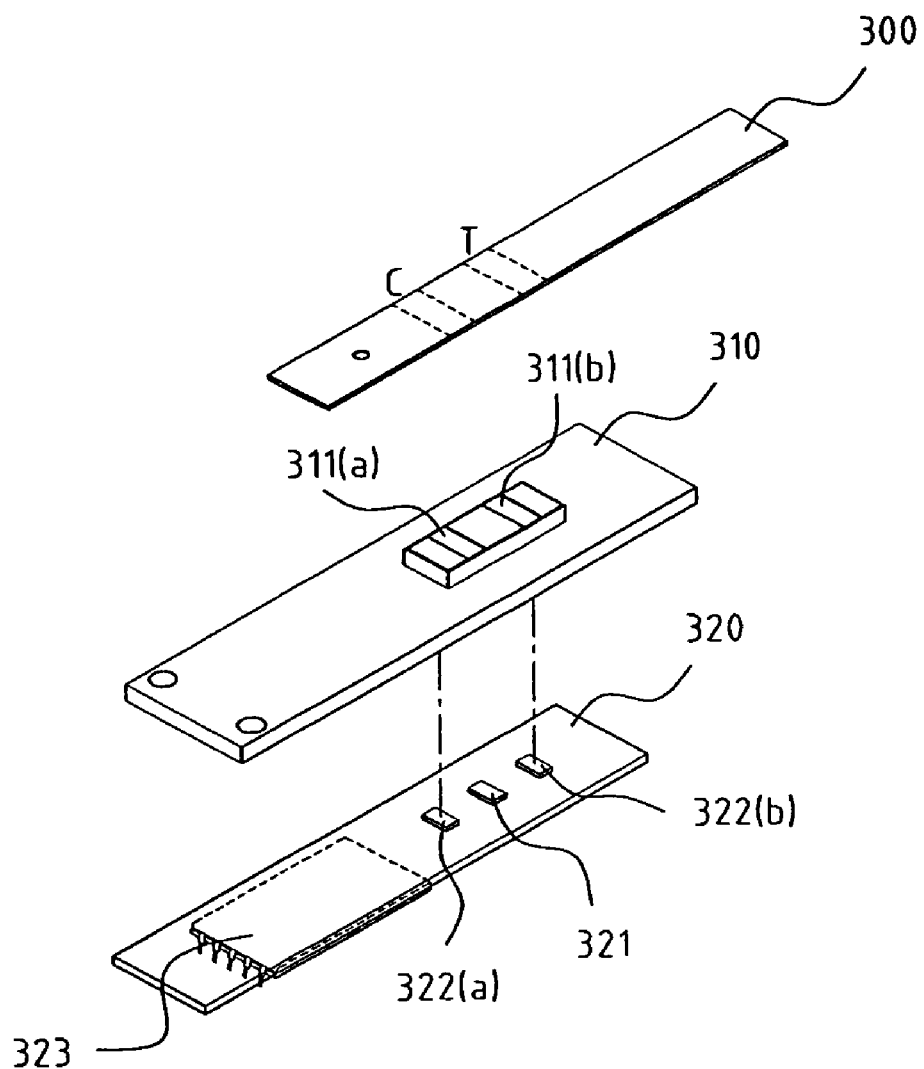
FIG. 3 is a schematic diagram illustrating an arrangement of internal components of an electronic testing apparatus according to an embodiment of the present invention.
Figure 4:
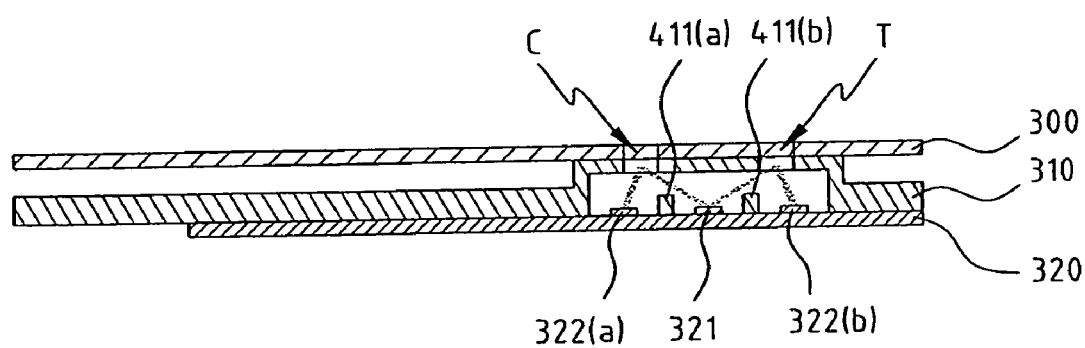
FIG. 4 is a cross-sectional view of an electronic testing apparatus illustrating the arrangement of the internal components according to an embodiment of the present invention.

FIG. 3 is a schematic diagram illustrating an arrangement of internal components of an electronic testing apparatus according to an embodiment of the present invention. FIG. 4 is a cross-sectional view of an electronic testing apparatus illustrating the arrangement of the internal components according to an embodiment of the present invention. Referring to FIG. 3, the electronic testing apparatus according to the embodiment of the present invention includes a testing paper 300, a light shelter 310, and a circuit board 320. There are two reaction lines, a C line and a T line, respectively, disposed on the testing paper 300. The C line represents a control line, and the T line represents a testing line. The C line reflects a quality and concentration standard of the test item. The test item may include physiological variation/disease inspection, such as pregnancy or kidney disease; drug test, such as benzodiazepine (BZD) drugs, marijuana, amphetamine, opium, etc. As shown in FIG. 4, the light shelter 310 includes a first sheltering member 411(a), and a second sheltering member 411(b), a first chamber, a second chamber, and a third chamber. The first sheltering member 411(a) separates the first chamber and the second chamber one from another. The second sheltering member 411(b) separates the second chamber and the third chamber one from another. The circuit board 320 includes a light source 321, a first detector 322(a), and a second detector 322(b) disposed thereon. The light source 321 is preferably a light emitting diode (LED) capable of emitting a green light or a yellow green light. The light source 321 is positioned between the first detector 322(a) and the second detector 322(b). The first chamber, the second chamber, and the third chamber respectively shelter the first detector 322(a), the light source 321, and the second detector (322b). The light shelter 310 further configures a first window 311(a) and a second window 311(b). The first reaction line and the second reaction line are well aligned to the first window 311(a) and 311(b), respectively.

Referring to FIG. 4, the light source 321 of the electronic testing apparatus is a non-directional light source. There is a first slit configured between a top of the first light sheltering member 411(a) and the light shelter 310. There is a second slit configured between a top of the second light sheltering member 411(b) and the light shelter 310. The first slit is reserved as a light transmitting path between the first chamber and the second chamber, and the second slit is reserved as a light transmitting path between the second chamber and the third chamber. A light emitted from the light source 321 is projected to the first window 311(a) through the first slit, and is also projected to the second window 311(b) through the second slit. The first detector 322(a) detects a reflected light of the light projected to the first window 311(a) through the first slit by the light source 321, and the second detector 322(b) detects a reflected light of the light projected to the second window 311(b) through the second slit by the light source 321. The first reaction line, C line, is a control line, and the second reaction line, T line, is a testing line.

The electronic testing apparatus according to the present invention further includes an IC controller 323 and a display 11 (not shown). The IC controller 323 is adapted for receiving detected signals respectively from the first detector 322(a) and the second detector 322(b), and therefore displaying a testing result on the display 11 according to the received detected signals.

Figure 5:
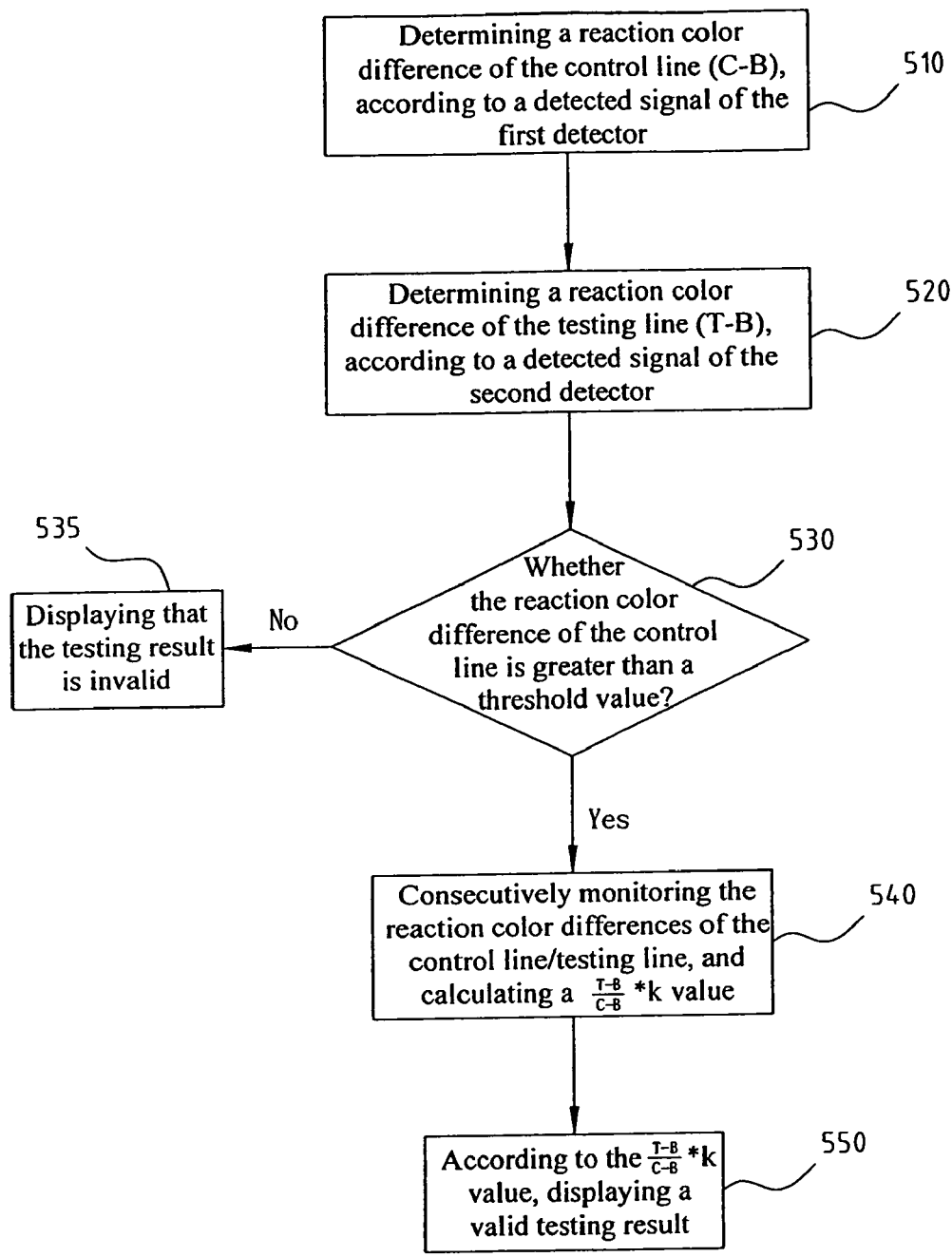
FIG. 5 is a flow chart illustrating a testing method for an electronic pregnancy testing apparatus as an embodiment of the present invention.

According to an embodiment of the present invention, the electronic testing apparatus is for pregnancy testing. Certainly, it can also be used to other rapid tests such as drug abuse, infection disease, etc. FIG. 5 is a flow chart illustrating a testing method for an electronic testing apparatus. Referring to FIG. 5, the testing method generally relies upon the IC controller 323 for obtaining a testing result according to the detected signals of the first detector 322(a) and the second detector 322(b). As shown in FIG. 5, at step 510, a reaction color difference between the C line and a light B is calculated according to the detected signal of the first detector 322(a), in which B is a background reflection light or a non-reacted light reflected by the C/T line, which is a predetermined internal parameter for the IC controller 323. Then, at step 520, a reaction color difference between the T line and the light B is calculated according to the detected signal of the second detector 322(b). At step 530, a validity of the testing result is determined according to the reaction color difference of the C line relative to the background reflecting light. In other words, if the reaction color difference of the C line relative to the background reflecting light is greater than a threshold value, the C line is considered as apparently existed, and the testing result is thus considered as valid, and therefore the process is further directed to step 540. Or otherwise, if the reaction color difference of the C line relative to the background reflecting light B is lower than the threshold value, the C line is considered as not existed, and the testing result is thus considered as invalid, and the process is further directed to step 535, in which the display 11 instructs that the test is invalid.

At step 540, in a preset period, preferably 3 minutes, the reaction color differences of the C line and the T line are consecutively monitored, and a first reaction color difference which is the reaction color difference of the C line relative to the background reflecting light B, and a second reaction color difference which is a reaction color difference of the T line relative to the background reflection light B. Then, a ratio between the second reaction color difference and the first reaction color difference is calculated. A feedback value is obtained as a product of the ratio times a return-to-zero coefficient k. And therefore, a valid testing result is displayed according to the feedback value.

Figure 6:
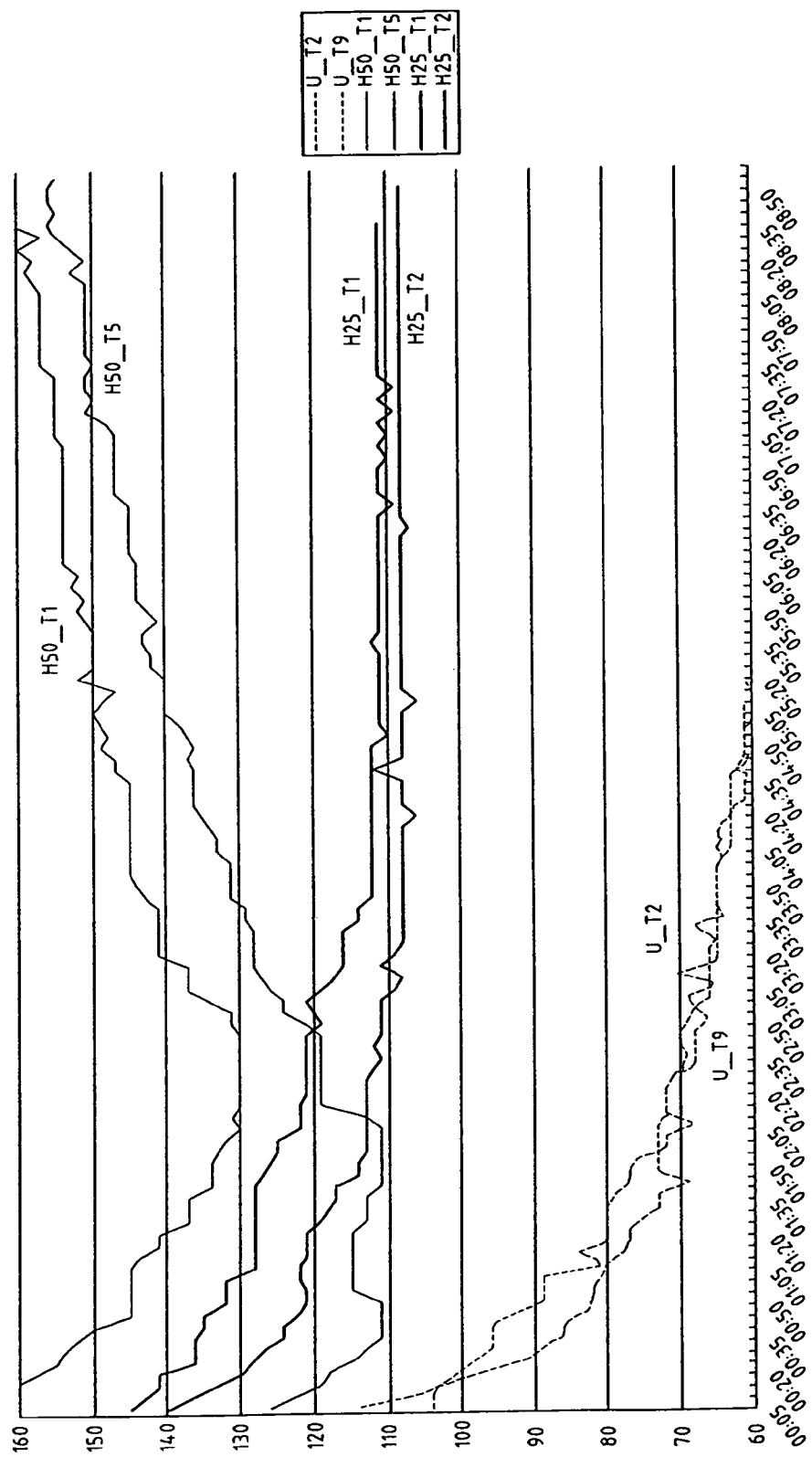
FIG. 6 is a graph including curves showing variations of feedback values corresponding to different HCG concentrations versus time.

FIG. 6 is a graph including curves showing variations of feedback values corresponding to different HCG concentrations versus time. As shown in FIG. 6, curves U_T2 and U_T9 represent a reference team composed of samples of water for reference. The curves H25_T1 and H25_T2 represent a testing team composed of samples of urine containing HCG of a concentration of 25 mIU/ml. The curves H50_T1 and H50_T5 represent a testing team composed of samples of urine containing HCG of a concentration of 50 mIU/ml. Two samples are picked from each team for testing. It can be learnt from FIG. 6, that a higher concentration of HCG corresponds to an earlier departure of the curve from that of the reference team. As can be seen starting from where corresponding to the third minute, differences of the testing team of 25 mIU/ml HCG and the testing team of 50 mIU/ml HCG from the reference team can be clearly identified, and thus displaying valid testing results.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An electronic testing apparatus, comprising:
    a testing paper, having a first reaction line and a second reaction line;
    a circuit board, having a light source, a first detector, and a second detector equipped thereon, wherein the light source is disposed between the first detector and the second detector; and
    a light shelter, defining a first chamber, a second chamber, and a third chamber, wherein there is a first slit configured between the first chamber and the second chamber, and a second slit configured between the second chamber and the third chamber;
    wherein the first chamber, the second chamber, and the third chamber respectively shelter the first detector, the light source, and the second detector, the first detector detects a reflected light of a light projected by the light source to the first window through the first slit, and the second detector detects a reflected light of the light projected by the light source to the second window through the second slit.

2. The electronic testing apparatus according to claim 1, wherein the first reaction line is a control line, and the second reaction line is a testing line.

3. The electronic testing apparatus according to claim 1, wherein the light shelter further defines a first window and a second window, and the first reaction line and the second reaction line are well aligned with the first window and the second window respectively.

4. The electronic testing apparatus according to claim 3, wherein the light source projects a light to the first window through the first slit.

5. The electronic testing apparatus according to claim 3, wherein the light source projects a light to the second window through the second slit.

6. The electronic testing apparatus according to claim 1, wherein the light source is a light emitting diode (LED).

7. The electronic testing apparatus according to claim 6, wherein the LED emits a green light.

8. The electronic testing apparatus according to claim 6, wherein the LED emits a yellow green light.

9. The electronic testing apparatus according to claim 1, wherein the circuit board further comprises a controller and a display equipped thereon.

10. The electronic testing apparatus according to claim 9, wherein the controller receives detected signals from the first detector and the second detector respectively, and displays a testing result on the display according to the received detected signals.

11. A testing method for the electronic testing apparatus, comprising:
    providing a light source positioned between a first detector and a second detector;
    disposing a first chamber, a second chamber, and a third chamber respectively sheltering the first detector, the light source, and the second detector, wherein a first slit is configured between the first chamber and the second chamber, and a second slit is configured between the second chamber and the third chamber;
    wherein the first detector detecting a reflected light of a light projected by the light source on a control reaction line of a testing paper through the first slit;
    the second detector detecting a reflected light of a light projected by the light source on a testing reaction line of the testing paper through the second slit; and
    obtaining a testing result according to detected signals of the first detector and the second detector.

12. The testing method according to claim 11, further comprising:
    determining a validity of the testing result by comparing a color difference of the testing reaction line with a threshold value according to the detected signals of the second detector.

13. The testing method according to claim 11, further comprising:
    determining the testing result according to a ratio between a color difference of the control reaction line determined by the detected signals of the first detector and the color difference of the testing reaction line determined by the detected signals of the second detector.

* * * * *